(12) United States Patent
Young

(10) Patent No.: US 10,363,188 B2
(45) Date of Patent: Jul. 30, 2019

(54) PATIENT MANEUVERING APPARATUS

(71) Applicant: Joy Oan Young, Fort Lauderdale, FL (US)

(72) Inventor: Joy Oan Young, Fort Lauderdale, FL (US)

(*) Notice: Subject to any disclaimer, the term of this patent is extended or adjusted under 35 U.S.C. 154(b) by 131 days.

(21) Appl. No.: 15/177,711

(22) Filed: Jun. 9, 2016

(65) Prior Publication Data

US 2017/0266072 A1 Sep. 21, 2017

Related U.S. Application Data

(60) Provisional application No. 62/309,719, filed on Mar. 17, 2016.

(51) Int. Cl.
*A61G 7/10* (2006.01)
*A61B 50/37* (2016.01)
(Continued)

(52) U.S. Cl.
CPC ............ *A61G 7/1023* (2013.01); *A61B 50/31* (2016.02); *A61B 50/37* (2016.02); *A61F 13/551* (2013.01);
(Continued)

(58) Field of Classification Search
CPC ....... A61G 7/10; A61G 7/1001–7/1011; A61G 7/1013; A61G 7/1023; A61G 7/1025;
(Continued)

(56) References Cited

U.S. PATENT DOCUMENTS 2,788,530 A * 4/1957 Ferguson .................. A61G 1/01
5/122
2,813,745 A * 11/1957 Frieder .................... B66C 1/127
294/77
(Continued)

FOREIGN PATENT DOCUMENTS

DE 202009012799 * 2/2010

OTHER PUBLICATIONS

Conceal. (n. d.) Collins English Dictionary—Complete and Unabridged, 12th Edition 2014. (1991, 1994, 1998, 2000, 2003, 2006, 2007, 2009, 2011, 2014). Retrieved Mar. 2, 2017 from http://www.thefreedictionary.com/conceal.*
(Continued)

*Primary Examiner* — Nicholas F Polito
*Assistant Examiner* — Amanda L Bailey
(74) *Attorney, Agent, or Firm* — Mark C. Johnson; Johnson | Dalal

(57) ABSTRACT

A patient maneuvering apparatus including a substantially planar body having a top surface, a bottom surface opposing the top surface, a left end, and a right end. The patient maneuvering apparatus also includes a first handle disposed at the left end of the body and a second handle disposed at the right end of the body, a mesh layer with a mesh layer thickness at least partially defining the bottom surface, a fabric layer of an absorbent material at least partially defining the top surface and with a fabric layer thickness, and a border spanning the perimeter of the body, surrounding the mesh and fabric layers, and with a border thickness greater than the mesh layer thickness and the fabric layer thickness.

12 Claims, 4 Drawing Sheets

(51) Int. Cl.
  *A61F 13/551* (2006.01)
  *A61F 17/00* (2006.01)
  *A61B 50/31* (2016.01)
  *A61F 13/15* (2006.01)
  *A61B 50/00* (2016.01)

(52) U.S. Cl.
  CPC ............ *A61F 17/00* (2013.01); *A61G 7/1051* (2013.01); *A61B 2050/0056* (2016.02); *A61B 2050/311* (2016.02); *A61F 2013/15121* (2013.01); *A61F 2013/15154* (2013.01); *A61G 7/1038* (2013.01)

(58) Field of Classification Search
  CPC .... A61G 7/1026; A61G 7/103; A61G 7/1038; A61G 7/1049; A61G 7/1051; A61G 7/1055; A61G 7/1057; A47G 9/0238; A47G 9/0246; A47G 9/0253; A47G 9/0261; B32B 2305/38; A01K 1/0606; A01K 73/02; A01K 77/00; A01K 29/00; A01K 13/00; B66C 1/127; B66C 1/18; A61B 50/31; A61B 50/37; A61F 13/551; A61F 17/00
  See application file for complete search history.

(56) References Cited

U.S. PATENT DOCUMENTS

| | | | | |
|---|---|---|---|---|
| 3,011,820 | A * | 12/1961 | Frieder | .................... D04G 1/00 294/77 |
| 3,829,914 | A * | 8/1974 | Treat | ..................... A47C 21/00 5/495 |
| 4,128,686 | A * | 12/1978 | Kyle | ........................ A61F 5/485 428/219 |
| 4,675,925 | A | 6/1987 | Littleton | |
| 4,723,327 | A | 2/1988 | Smith | |
| 4,823,418 | A * | 4/1989 | Downs | ................... A61B 17/42 182/138 |
| 4,872,226 | A | 10/1989 | Lonardo | |
| 4,938,607 | A * | 7/1990 | Kelley | ................... B65D 31/00 190/1 |
| 4,944,057 | A | 7/1990 | Shaw | |
| 5,138,731 | A | 8/1992 | Harcrow, Jr. | |
| 5,148,558 | A | 9/1992 | Dunn | |
| 5,263,495 | A | 11/1993 | Butterfield | |
| 5,396,670 | A * | 3/1995 | Firebaugh | ............ A61G 7/1017 5/89.1 |
| 5,442,821 | A | 8/1995 | Weeks | |
| 5,615,426 | A * | 4/1997 | Hokett | .................. A61G 7/1017 5/486 |
| 5,920,929 | A * | 7/1999 | Hensley | ............... A61G 7/1023 5/485 |
| 5,978,989 | A * | 11/1999 | Chavez | .................... A61G 1/01 294/140 |
| 6,196,229 | B1 | 3/2001 | Piazza | |
| 6,631,697 | B1 * | 10/2003 | Solze | ................... A01K 1/0263 119/728 |
| 6,671,899 | B1 * | 1/2004 | Oja | ...................... A61G 7/1023 5/89.1 |
| 6,908,131 | B2 | 6/2005 | Main et al. | |
| D611,670 | S * | 3/2010 | Booth | .............................. D34/1 |
| 7,818,836 | B2 | 10/2010 | Stinson | |
| 7,926,860 | B2 | 4/2011 | Hill et al. | |
| 8,701,225 | B1 | 4/2014 | Latiff | |
| 2005/0055769 | A1 | 3/2005 | Taylor | |
| 2007/0056096 | A1 | 3/2007 | Assink | |
| 2013/0042409 | A1 * | 2/2013 | Gil Gomez | .......... A47G 9/0246 5/487 |
| 2013/0152304 | A1 * | 6/2013 | Dovervik et al. | ....... A61G 7/10 5/89.1 |
| 2013/0227789 | A1 * | 9/2013 | Olson | .................... A61G 1/013 5/625 |
| 2017/0056268 | A1 * | 3/2017 | Bullock | ............... A61G 7/1055 |

OTHER PUBLICATIONS

Doctors Foster and Smith. (Jun. 6, 2012). ComfortLift Carrier. http://www.drsfostersmith.com/product/prod_display.cfm?pcatid=8082 (Year: 2012).*

DE 202009012799 English translation of abstract (Year: 2010).*

* cited by examiner

300

300

PATIENT MANEUVERING APPARATUS

This application claims priority to U.S. Provisional Patent Application No. 62/309,719 filed Mar. 7, 2016, the entirety of which is incorporated by reference.

FIELD OF THE INVENTION

The present invention relates generally to apparatuses used to maneuver bed-ridden individuals, and, more particularly, relates to a portable apparatus used to maneuver bed-ridden patients.

BACKGROUND OF THE INVENTION

There are many known devices and apparatuses used to maneuver a user or patient confined to a bed or other location, wherein the user or patient has limited mobility. Some of these devices have a unitary piece of fabric with multiple apertures at opposing ends. These multiple apertures act as handles for two individuals to grasp on. These devices are problematic for multiple reasons. First, these devices require two users to move the bed-ridden individual, which is neither cost-effective for larger health care institutions, nor possible for single care givers of those bed-ridden individuals. These devices also do not provide the flexible rigidity needed to comfortably and effectively move the patient. What is meant by flexible rigidity is a device's ability to flex, yet sufficiently support and disperse the weight of the patient at certain locations of the device to provide maximum leverage used to move the patient.

Moreover, as many bed-ridden individuals experience incontinence, these devices also fail to provide users the ability to continually place the device under the patient (if desired). Even when continually placed under the patient, these devices also fail to provide a means for the user to effectively permit the capture and/or transfer of urine and other matter from the patient in an effective, safe, and comfortable way. Said another way, the structure and design of many of these devices do not provide users the ability to thwart or inhibit the generation of bed sores.

Therefore, a need exists to overcome the problems with the prior art as discussed above.

SUMMARY OF THE INVENTION

The invention provides a patient maneuvering apparatus that overcomes the hereinafore-mentioned disadvantages of the heretofore-known devices and methods of this general type and that provides an apparatus that may be utilized by a single user to transfer and/or move a bed-ridden patient. In addition, the apparatus may also be continually placed underneath the patient to enable mobility at any time desired by the user.

With the foregoing and other objects in view, there is provided, in accordance with the invention, a patient maneuvering apparatus including a substantially planar body having a top surface, a bottom surface opposing the top surface, a left end, and a right end, a first handle disposed at the left end of the body and a second handle disposed at the right end of the body, a mesh layer including a mesh layer thickness at least partially defining the bottom surface, a fabric layer of an absorbent material at least partially defining the top surface, the fabric layer including a fabric layer thickness; and a border spanning a perimeter of the body, surrounding the mesh and fabric layers, and with a border thickness greater than the mesh layer thickness and the fabric layer thickness.

In accordance with another feature, an embodiment of the present invention includes the border having a first end and a second end opposing the first end and the border is made of a strip of continuous and joint-free material spanning from the first end to the second end.

In accordance with a further feature of the present invention, the border defines the first and second handles.

In accordance with a further feature of the present invention, the border is of a fabric material In accordance with another feature, an embodiment of the present invention also includes the mesh layer, the fabric layer, and the border are of different materials.

In accordance with yet another feature, an embodiment of the present invention includes the mesh layer is in fluid communication with the fabric layer.

In accordance with a further feature of the present invention, an embodiment of the present invention includes a patient maneuvering apparatus having a user support body including a body contact surface, a bottom surface opposite the body contact surface, a left end, and a right end opposite the left end, a first user support handle disposed at the left end of the user support body, a second user support handle disposed at the right end of the user support body, a first layer of an absorbent material at least partially defining the body contact surface, the first layer including a first layer thickness, a second layer of a web material at least partially defining the bottom surface, the second layer including a second layer thickness, and a border substantially surrounding a perimeter of the user support body, the border having at least a portion concealed by the first layer and including a border thickness greater than the first layer thickness and the second layer thickness.

In accordance with a further feature of the present invention, the border is of a fabric material.

In accordance with another feature, an embodiment of the present invention also includes the border having a first end and a second end opposing the first end and the portion of the border concealed by the first layer is the first end and the second end.

In accordance with a further feature of the present invention, the border includes a first end and a second end opposing the first end and the border is made of a strip of material having a smooth and continuous upper surface spanning from the first end to the second end.

In accordance with a further feature of the present invention, the first layer, the second layer, and the border are of different materials.

In accordance with another feature of the present invention, the first and second user support handles are defined by the border.

In accordance with yet another feature of the present invention, the first and second user support handles are defined by the border.

In accordance with a further feature of the present invention, the first layer thickness and the second layer thickness are less than 0.10 inches and the border thickness is approximately 0.20 to 0.40 inches.

Although the invention is illustrated and described herein as embodied in a patient maneuvering apparatus it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to a direction of the apparatus spanning from the opposing ends where the handles are respectively located.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

Figure 1:
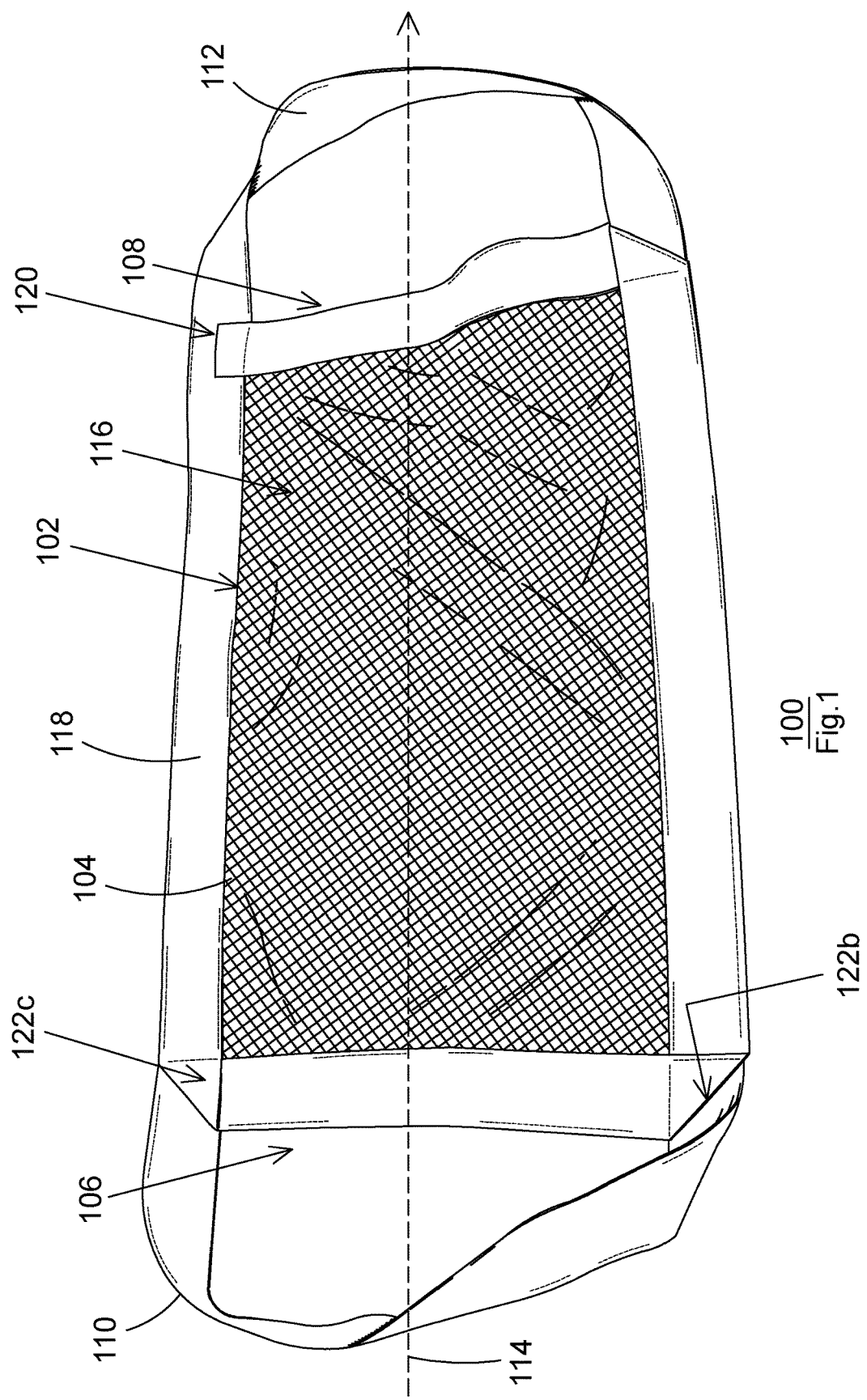
FIG. 1 is a plan view of a bottom surface of a patient maneuvering apparatus in accordance with the present invention.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

Figure 2:
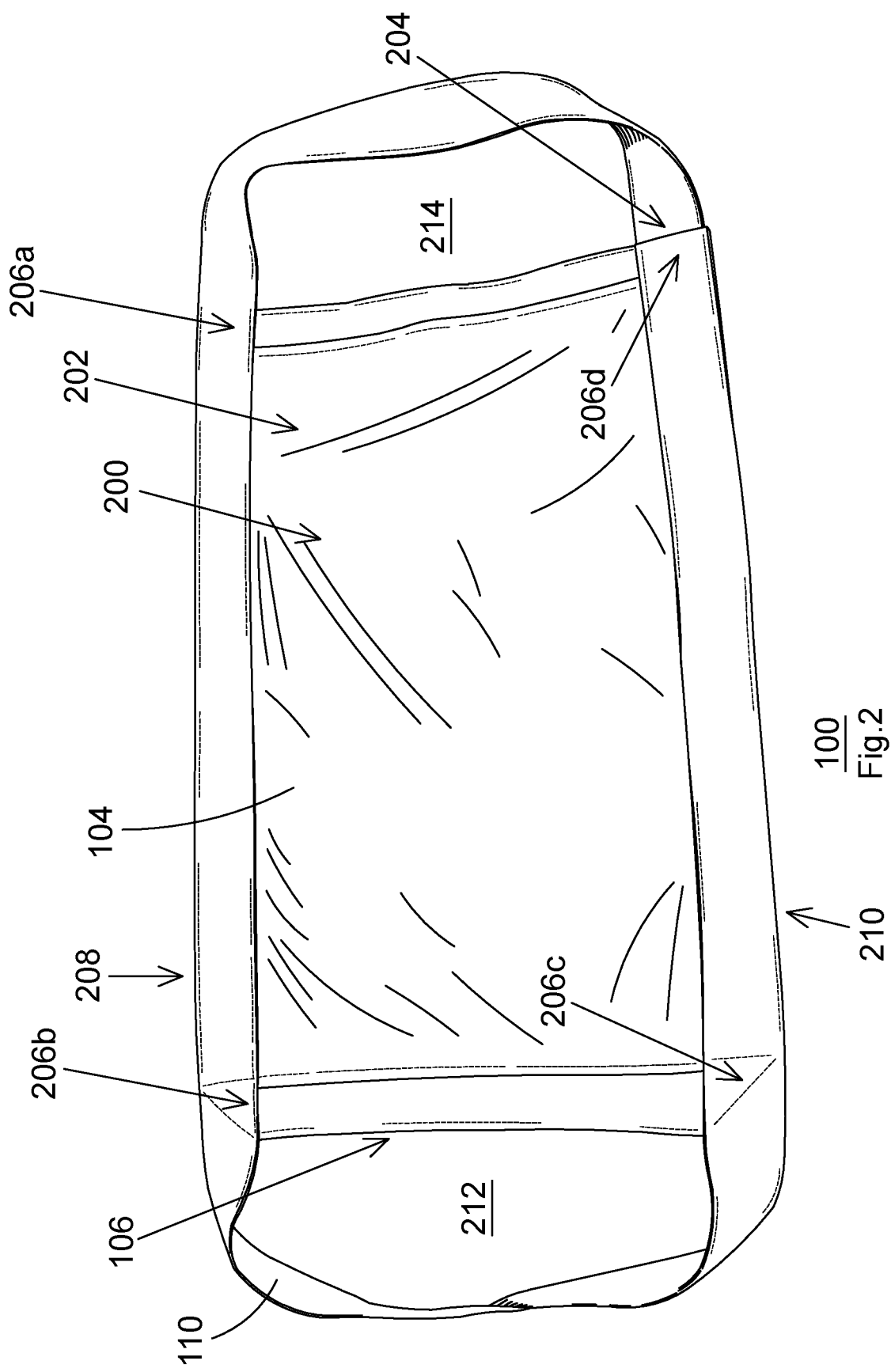
FIG. 2 is a top plan view of a top surface of the patient maneuvering apparatus of FIG. 1 in accordance with the present invention.

The present invention provides a novel and efficient patient maneuvering apparatus 100. Referring now to FIGS. 1-2, one embodiment of the present invention is shown in top plan views. More specifically, FIG. 1 depicts a top plan view of the bottom surface 102 and FIG. 2 depicts a top plan view of the top surface 200 of the apparatus 100. FIG. 1 shows several advantageous features of the present invention, but, as will be described below, the invention can be provided in several shapes, sizes, combinations of features and components, and varying numbers and functions of the components. Moreover, the bottom and top surfaces 102, 200 may also be interchanged in accordance with other embodiments of the present invention and the desired use of the apparatus 100.

The apparatus 100 can be seen having a substantially planar body 104, i.e., a relatively flat profile for the body 104 that is generally not to exceed 2-3 inches in overall height. As such, the apparatus may be comfortably and effectively placed underneath the patient when desired for use and even when not desired for use. The apparatus 100 can also been seen having a left end 106 and a right end 108. Of course the perspective of the apparatus 100 may change depending on the viewpoint, such that the left end 106 may, for all practical purposes depending on the viewpoint, be considered to be the right end 108. The top and bottom surfaces 200, 102 may also be considered to oppose one another, i.e., located on opposite sides of the apparatus 100.

The apparatus 100 can also be seen with a first handle 110 disposed at the left end 106 of the body 104 and a second handle 112 disposed at the right end 108 of the body 104. The term "handle" is hereinafter defined as something that is designed or intended to be held or grasped by a user's hand. This may include material defining an aperture shaped and sized to receive a user's hand or a ridge shaped and sized to permit a user to grasp. In preferred embodiments, the apparatus 100 includes two opposing strap handles 110, 112 that project outwardly from the respective ends 106, 108. The handles 110, 112 may include a single pair of handles that are disposed, or have a user-grasping portion disposed, at the substantial center of mass of the body 104 so as ensure a proportionally equivalent amount of force was supplied from the apparatus to the individual desired to be moved. Said another way, the handles 110, 112 are disposed, or have a user-grasping portion disposed, at the longitudinal center axis (depicted by line 114) of the body 104. As such, the apparatus 100 beneficially provides the user the ability to maneuver or roll the patient with one hand, while having the other hand free to clean the patient or the area underneath the patient. This can be especially beneficial for a user who is relatively small in comparison to the patient. The user may also be alleviated of the need to wear a support apparatus, e.g., a hernia belt, when maneuvering or rolling the patient. In one embodiment, the handles 110, 112 include a length of between approximately 22-24 inches in length. In other embodiments, the length of the handles may be outside of this range.

The apparatus may also be seen having a mesh layer 116 with a mesh layer thickness at least partially defining the bottom surface 102 and a fabric layer 202 of an absorbent material at least partially defining the top surface 200 and with a fabric layer thickness. As depicted in FIG. 1, because of the mesh layer 116, the fabric layer 202 is in fluid communication with the mesh layer 116. Said another way, should the fluid pass through the absorbent fabric layer 202, it will then pass through the mesh layer and to an area or location where it can accumulate outside of the contact with the user, thereby decreasing the likelihood of generating environmental conditions that would cause the user to experience bed sores. Alternatively, should the mesh layer 116 be placed at the bottom surface 102 and because the mesh layer 116 is a collection of interlaced material each defining apertures for fluids and other materials of the user to pass through, the fabric layer 202 is able to be accessed from the top surface 102 of the apparatus 100. In one embodiment, the fabric layer is of an absorbent material such as 100% cotton, a high-cotton/polyester blend, or wool. In other embodiments, the material of the fabric layer 202 may be flax, hemp, synthetic fibers, or the like. The mesh layer 116, which may include a plurality of interlaced or woven fibers defining equal-spaced apertures, may be of a polymeric material, e.g., PVC, or may also be of a metallic material such as stainless steel. In other embodiments, the mesh layer 116 may be of a composite or ceramic material with a viscous or water-resistant film applied thereto to minimize frictional resistance and/or discomfort to the patient.

The apparatus 100 can also be seen having a border 118 spanning the perimeter of the body 104, surrounding the mesh and fabric layers 116, 202, and with a border thickness greater than the mesh layer thickness and fabric layer thickness. As such, the thickness of the border 118 provides rigidity to the body 104, thereby providing stability to the apparatus 100 when in use. The border 118 also acts as the point-of-contact with the patient when the user applies a lifting force to the apparatus through the handles 110, 112. In one exemplary embodiment, the thickness of the mesh and fabric layers 116, 202 are less than approximately 0.10 inches, while the thickness of the border 118 is approximately 0.25 inches. Other various thickness are contemplated and within the scope of the present invention. The border 118 can also be said to be denser, in some embodiments, than the fabric or mesh layers. In one embodiment, the apparatus has a longitudinal length of approximately 2-3 feet and a width of 1-2 feet, while said length and width may be greater than or less than said ranges in other embodiments depending on the design application. Furthermore, the border 118 may be approximately 2-3 inches in width, or may be outside of said range.

In one embodiment, the border 118 is defined by one or more individuals strips of woven fabric material sewn together to surround the mesh and fabric layers 116, 202 and act as a perimeter to the body 104 (as depicted in FIG. 2). In one embodiment the border 118 material is of a pure cotton or cotton/polyester blend. In other embodiments, the material may vary. The handles 110, 112 may also consist of the same material used to create the border 118 and may also be sewn or otherwise coupled to the body 104. In other embodiments, the border 118 includes a first end 120, a second end 204 opposing the first end 120, and is of a strip of material separating the first and second end 204 of the border 118, wherein the strip of material is continuous and joint-free. Said another way, to ensure the structure rigidity and integrity of the apparatus 100, the border 118 is formed by a single piece of strip material that is folded and mitered at the desired points, e.g., locations 122a-n (where "n" represents any number greater than 1), to create the perimeter of the body 104. The strip of material is "joint-free" in that there are no separate pieces of material defining the border, i.e., so there are no joints. The strip of material defining the border 118 may be approximately 5 yards in length (from the first end 120 to the second end 204) to define an apparatus having a total length of approximately 2-3 feet and a width of approximately 1-2 feet.

As shown in FIGS. 1 and 2, the strip of material forming the border 118 is folded and mitered at locations 122a-c and then continues to form the handle 112. The strip of material continues (as shown in FIG. 2) to the top surface 200 wherein it can be seen sewn to itself at various locations 206a-n and forms the handle 110. The border 118 can be seen advantageously thicker at the upper and lower ends 208, 210 of the apparatus 100 to again provide structural rigidity and integrity to the apparatus. The apparatus 100 is also flexible, in that is capable of repeated (i.e., more than 1000 times) bending (i.e., positions with approximately 180° orientations) without plastic deformation or otherwise breaking the apparatus 100.

The present invention may also be utilized to help disabled individuals ("user") with loss of use in one of their arms to roll out of bed. For example, the user may place the front or back surface 200, 102 of the apparatus 100 against his or her chest (or back), in addition to placing his or her disabled arm through one of the apertures 212, 214 defined by the handles 110. The user may then pull the other side of the apparatus 100 where the disabled arm is not placed, to cause rotation of the user's body. Similarly, a method of maneuvering a disabled user's leg(s) may also be utilized wherein the user's leg(s) are placed on the front or back surfaces 200, 102.

Figure 3:
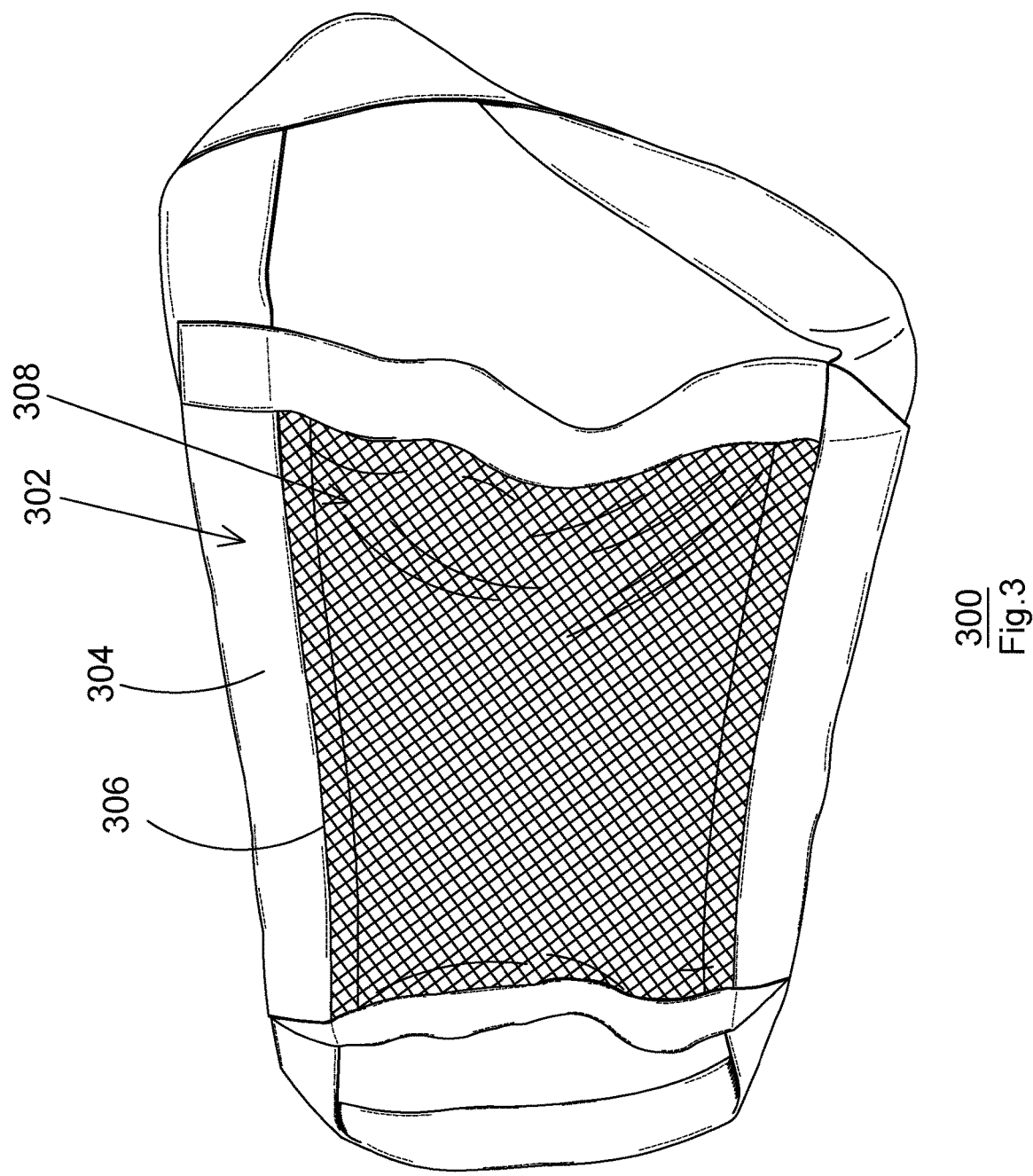
FIG. 3 is a perspective view of the bottom surface of a patient maneuvering apparatus in accordance with another embodiment of the present invention.
Figure 4:
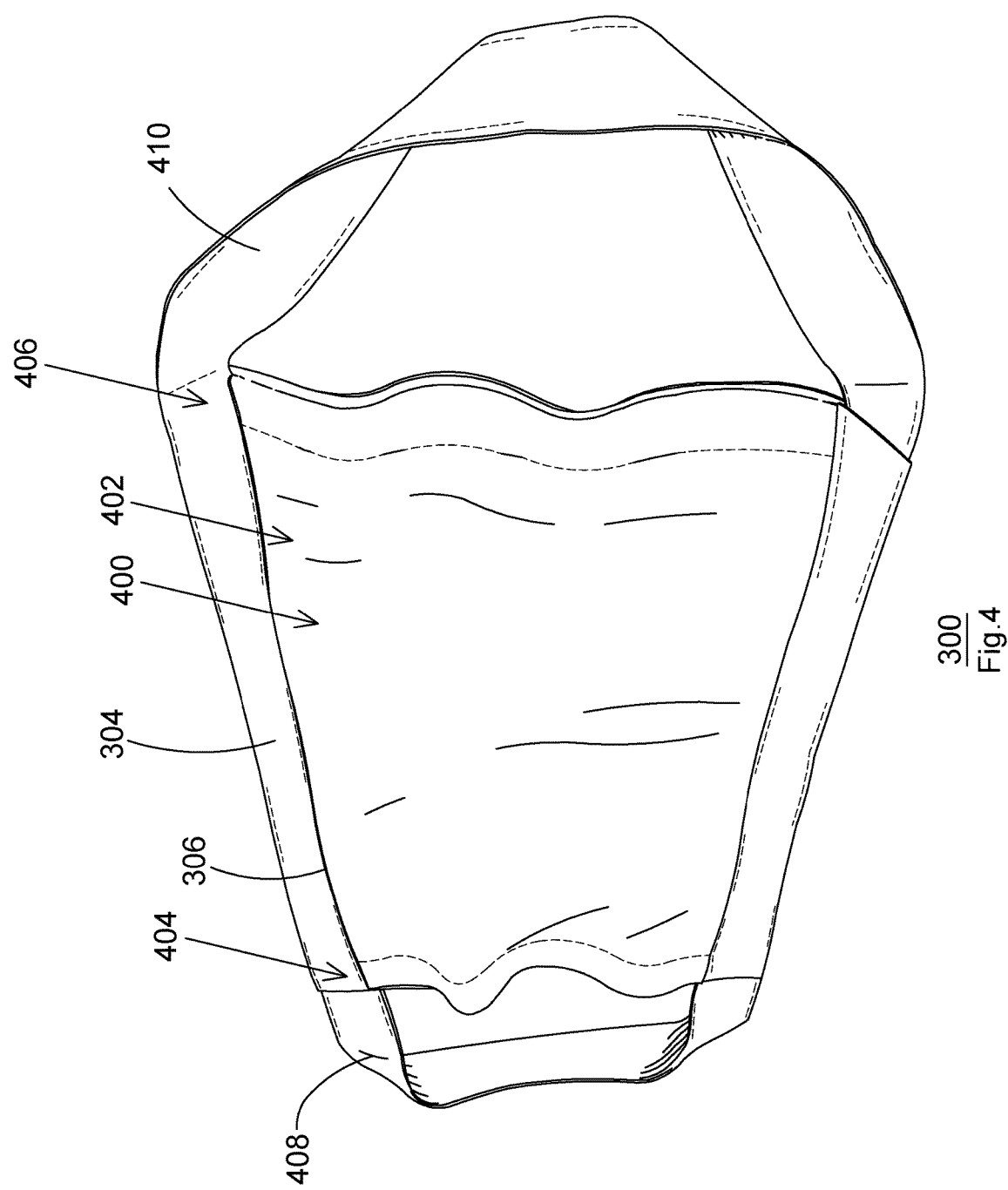
FIG. 4 is a perspective view of the top surface of the patient maneuvering apparatus of FIG. 3.

With reference now to FIGS. 3-4, another embodiment of a patient maneuvering apparatus 300 is shown in perspective views. More specifically, FIG. 3 is a perspective view of a bottom surface 302 and FIG. 4 is a perspective view of a body contact surface 400, i.e., top surface of the apparatus 300. In one embodiment, the apparatus 300 includes the same or substantially similar features as those described above with respect to the apparatus 100, with the exception of differences among the borders. More specifically, the apparatus 300 includes a portion of the border 304 being concealed by a first layer 402 so that the border 304 provides additional comfort when contacting a user's skin, as will be explained in further detail below. In other embodiments, the apparatus 300 may have additional differentiating features. Similar to that described with respect to the apparatus 100, the bottom and top surfaces 302, 400 of the apparatus 300 may also be interchanged in accordance with other embodiments of the present invention and the desired use of the apparatus 300. In the same vein, similar to that described with respect to the apparatus 100, in one embodiment, the apparatus 300 has a length of approximately 2-3 feet and a width of approximately 1-2 feet. In other embodiments, the length and/or the width may be outside of these ranges.

With specific reference to FIG. 4, the border 304 is depicted substantially surrounding a perimeter of a user support body 306. The term "substantially surrounding" is defined herein as surrounding, i.e., contouring, at least 50%-60% of the perimeter of the user support body 306. For example, a user may choose to omit the border 304 along a first end 404 and/or a second end 406 of the user support body 306. In other embodiments, the border 304 may completely surround the user support body 306.

In a preferred embodiment, the border 304 is a strip of material that extends from the first end 404 to the second end 406 and includes a smooth and continuous upper surface. Said another way, to ensure the structural rigidity and integrity of the apparatus 300, the border 304 is formed by a single piece of strip material that may be folded and mitered at desired locations around a perimeter of the user support body 306, similar to the matter described above with respect to the apparatus 100. The strip of material is "continuous" in that there are no separate pieces of material defining the border 304, i.e., there are no joints or linkages. In other embodiments, the border 304 may be made of more than one strip of material and may include joints or linkages coupling the pieces of material to each other. In one embodiment, the border 304 defines a first handle 408 and a second handle 410 having similar features to the handles 110, 112 described above with respect to FIG. 1. In other embodiments the first and second handles 408, 410 may be defined by alternative pieces of material.

In one embodiment, the user support body 306 includes a relatively level profile that is generally not to exceed 2-3 inches in overall height. As such, the height effectuates the comfortable placement of the apparatus 300 underneath the user when desired for use or when not in use and stored by the user. In other embodiments, the height of the user support body 306 may be outside of this range.

In order to provide increased comfort to the user when the apparatus 300 is placed underneath the user, in one embodiment, the portion of the border 304 that is concealed by the first layer 402 may be the first end 404 and the second end 406 of the user support body 306. As such, the border 304 does not to come into contact with the user's skin. This may be especially advantageous for users whom have delicate skin that is prone to irritation, bruising, tearing or users whom are experiencing bed sores. In another embodiment, only one of either the first end 404 or the second end 406 may be concealed by the first layer 402. In other embodiments, additional portions of the border 304 may be concealed by the first layer 402.

With reference again to FIGS. 3 and 4, the first layer 402 is of an absorbent material at least partially defining the body contact surface 400 and the second layer 308 is of a web material at least partially defining the bottom surface 302. In one embodiment, the first and second layers 402, 308 include the same features as the fabric layer 202 and the mesh layer 116, thus providing the same benefits, as those described above with respect the fabric layer 202 and the mesh layer 116. More specifically, as described above, should the fluid pass through the first layer 402, it will then pass through the second layer 308 and to an area or location where it can accumulate outside of the contact with the user, thereby decreasing the likelihood of the user experiencing bed sores. In other embodiments, the first and second layers 402, 308 may include different features than those described with respect to the fabric layer 202 and the mesh layer 116.

In one embodiment, the border 304 may include a border thickness greater than a thickness of either or both of the first and second layers 402, 308. In one embodiment, the border thickness may be approximately 0.25-0.40 inches and the thickness of either or both the first and second layers 402, 308 may be less than approximately 0.10-0.15 inches. As such, the thickness of the border 304 provides rigidity to the support body 306, providing stability to the apparatus 300 when in use. As one of ordinary skill in the art can appreciate, various thicknesses are contemplated and within the scope of the present invention.

A patient maneuvering apparatus has been disclosed that features a substantially planar body having a top surface, a bottom surface opposing the top surface, a left end, and a right end. In one embodiment, a first handle is disposed at the left end of the body and a second handle disposed at the right end of the body. The patient maneuvering apparatus may also include a mesh layer having a mesh layer thickness at least partially defining the bottom surface, a fabric layer of an absorbent material at least partially defining the top surface, the fabric layer including a fabric layer thickness, and a border spanning a perimeter of the body, surrounding the mesh and fabric layers, and with a border thickness greater than the mesh layer thickness and the fabric layer thickness. Other features of the invention have been disclosed, but are not limited to the particular details disclosed herein.

What is claimed is:

1. A patient maneuvering apparatus comprising: a substantially planar body having a perimeter, a top surface, a bottom surface opposing the top surface, a length and a width, a left end of the length, and a right end of the length; a mesh layer including a mesh layer thickness at least partially defining the bottom surface; a fabric layer of an absorbent material at least partially defining the top surface, the fabric layer including a fabric layer thickness; and a strip of continuous material defining a border, a first handle, and a second handle, the border spanning the perimeter of the body, surrounding the mesh and fabric layers, and with a border thickness greater than each of the mesh layer thickness and the fabric layer thickness; the strip of continuous material is sewn to the planar body about the perimeter and is folded and mitered at at least three points around the perimeter, and the strip of continuous material is sewn to the planar body at the points where it is folded and mitered, the first handle defining a first aperture sized and shaped to receive at least a portion of a user's hand at the left end and having a length that is longer than, and which spans, the width of the planar body, and the second handle defining a second aperture sized and shaped to receive the at least a portion of a user's hand at the right end and having a length that is longer than, and which spans, the width of the planar body.

2. The patient maneuvering apparatus of claim 1, wherein: strip of continuous material is made of a fabric material.

3. The patient maneuvering apparatus of claim 1, wherein: the mesh layer, the fabric layer, and the strip of continuous material are made of different materials.

4. The patient maneuvering apparatus of claim 1, wherein: the mesh layer is in fluid communication with the fabric layer.

5. A patient maneuvering apparatus comprising: a user support body having a perimeter around a length and width of the user support body, a body contact surface, a bottom surface opposite the body contact surface, a left end of the length, and a right end of the length opposite the left end; a first layer of an absorbent material at least partially defining the body contact surface, the first layer including a first layer thickness; a second layer of a mesh material at least partially defining the bottom surface, the second layer including a second layer thickness; and a singular strip of continuous material defining a border, a first user support handle, and a second user support handle, the border substantially surrounding a perimeter of the user support body, and having at least a portion disposed beneath the first layer and including a border thickness greater than the first layer thickness and the second layer thickness, the first user support handle defining a first aperture sized and shaped to receive at least a portion of a user's hand at the left end and having a length that is longer than and which spans, the width of the user support body, the second user support handle defining a second aperture sized and shaped to receive the at least a portion of a user's hand at the right end and having a length that is longer than, and which spans the width of the user support body, and the strip of continuous material sewn to the planar body about the perimeter and folded and mitered at at least three points around the perimeter, and the strip of continuous material sewn to the planar body at the points where it is folded and mitered.

6. The patient maneuvering apparatus of claim 5, wherein: the border is made of a fabric material.

7. The patient maneuvering apparatus of claim 5, wherein:
- the singular strip of continuous material includes a first end and a second end opposing the first end; and
- the portion of the border disposed beneath the first layer is at least one of the first end and the second end of the singular strip of continuous material.

8. The patient maneuvering apparatus of claim 7, wherein: the singular strip of continuous material has a continuous upper surface spanning from the first end to the second end.

9. The patient maneuvering apparatus of claim 5, wherein: the first layer, the second layer, and the singular strip of continuous material are made of different materials.

10. The patient maneuvering apparatus of claim 5, wherein:
- the first layer thickness and the second layer thickness are less than 0.10 inches; and
- the border thickness is approximately 0.20 to 0.40 inches.

11. A patient maneuvering apparatus, comprising: a substantially planar body having a perimeter, a length, and a width, the length defining a first end and a second end, the planar body having a mesh layer including a mesh layer thickness and defining a bottom surface of the planar body, the planar body further having a fabric layer including a fabric layer thickness and comprised of an absorbent material at least partially defining a top surface of the planar body; a first handle at the first end of the planar body formed of a strip of fabric that spans the width of the planar body at the first end of the planar body, and which has a length that is longer than the width of the first end of the planar body; a second handle at the second end of the planar body formed of a strip of fabric that spans the width of the planar body at the second end of the planar body, and which has a length that is longer than the width of the second end of the planar body; and a strip of continuous fabric material: defining a border, the strip of fabric of the first handle, and the strip of fabric of the second handle, the border spanning the perimeter of the body, surrounding the mesh layer and the fabric layer of the planar body, and with a border thickness greater than each of the mesh layer thickness and the fabric layer thickness; and wherein the strip of continuous fabric material is coupled to the planar body around the perimeter and folded and mitered at at least three points around the perimeter, the strip of continuous material sewn to the planar body at the three points where it is folded and mitered.

12. The apparatus of claim 11, wherein the length of the planar body is not more than three feet, and the width is not more than two feet.

* * * * *